United States Patent [19]

Banauch et al.

[11] 3,964,974

[45] June 22, 1976

[54] ENZYMATIC DETERMINATION OF GLUCOSE

[75] Inventors: Dieter Banauch; Wolfgang Brümmer; Wolfgang Ebeling; Roland Helger; Norbert Hennrich; Hermann Lang, all of Darmstadt, Germany

[73] Assignee: Merck Patent Gesellschaft mit beschrankter Haftung, Darmstadt, Germany

[22] Filed: Sept. 10, 1973

[21] Appl. No.: 395,547

[30] Foreign Application Priority Data
Sept. 28, 1972 Germany............................ 2247608

[52] U.S. Cl............................ 195/103.5 C; 195/63; 195/99; 195/103.5 R
[51] Int. Cl.² ...................... G01N 31/14; C07G 7/02
[58] Field of Search............... 195/103.5 R, 103.5 C, 195/99, 63

[56] References Cited
UNITED STATES PATENTS

| 3,290,228 | 12/1966 | Gretton et al............ | 195/103.5 C X |
| 3,335,069 | 8/1967 | Wachter..................... | 195/63 X |
| 3,413,198 | 11/1968 | Deutsch..................... | 195/103.5 R |
| 3,703,591 | 11/1972 | Bucolo et al................ | 195/103.5 R |
| 3,764,478 | 10/1973 | Bergmeyer et al........... | 195/103.5 R |

OTHER PUBLICATIONS

Miwa, et al., Matarotase Effect on Colorimetric Determination of Blood Glucose With B–D–Glucose Oxidase, Clin. Chim. Acta, vol. 37, Mar. 1972, (pp. 538–540).

Metzger, et al., Subcellular Distribution and Properties of Hepatic Glucose Dehydrogenase of Selected Vertebrates, J. of Biological Chemistry, vol. 240, No. 7, 1965, (pp. 2767–2771).

Sadoff, et al., Significance of Multiple Forms of Glucose Dehydrogenase in Relation to Its Heat Resistance, The Spores, III, 1965 (pp. 97–110).

Primary Examiner—David M. Naff
Attorney, Agent, or Firm—Millen, Raptes & White

[57] ABSTRACT

Glucose is rapidly ad quantitatively determined with an analytical agent containing glucose dehydrogenase having an activity of at least 2 $\mu$/mg and $NADH_2$ oxidase activity less than 0.1%, a pyridine coenzyme, a buffer and mutarotase to increase spontaneous mutarotation of alpha-glucose to beta-glucose. There may be optionally present inhibitors for reduced pyridine coenzyme oxidases and a thermal stabilizing amount of alkali metal chloride.

10 Claims, No Drawings

3,964,974

ENZYMATIC DETERMINATION OF GLUCOSE

BACKGROUND OF THE INVENTION

This invention relates to improved agents for the enzymatic determination of glucose.

The most important routine analysis in a clinical laboratory is blood sugar determination. This analysis is used for the detection and therapeutic control of diabetes mellitus and for the diagnosis of several other metabolic diseases.

Specific methods are required for the quantitative determination of blood sugar. The oldest methods of analysis are based on the reduction capacity of glucose, wherein substances such as potassium hexacyanoferrate III, picric acid, or copper(II) ions in an alkaline solution are employed as oxidizing agents. However, because this technique, when employed in connection with body fluids, detects all other reducing substances, e.g., creatine, creatinine, uric acid, ascorbic acid and glutathione, its lack of specificity no longer satisfies present requirements.

Another group of determination methods is based on the formation of furan derivatives from glucose, employing the water-liberating effect of concentrated acids, and the furans thereafter are reacted with aromatic amines, such as, for example, o-toluidine, to form dyes. Although this method is widely utilized as a routine analysis, the specificity thereof leaves much to be desired since, in addition to glucose, all other aldoses also participate in the reacion. A grave disturbance of this test occurs when determining glucose in the serum of patients who received infusions of dextran based plasma expanders, which causes turbidity in the test mixture. Also, the determination is rendered troublesome and time- consuming by the step of boiling with acid, which is required for condensation purposes.

In addition to this so-called o-toluidine method, two enzymatic processes are customarily employed for the determination of glucose, viz., the glucose oxidase method and the hexokinase method.

In the glucose oxidase method, the glucose is oxidized by oxygen to gluconic acid with glucose oxidase catalysis, thus producing hydrogen peroxide which, in turn, oxidizes a colorless chromogen to a dye in a catalyzed secondary reaction. As the catalyst in the secondary reaction, peroxidase can be utilized. A frequently employed chromogen is o-dianisidine. The glucose oxidase is specific for glucose but the secondary reaction is disturbed by substances which consume hydrogen peroxide. In body fluids, especially interfering are uric acid, ascorbic acid and catalase. Additional disadvantages are the long duration of the analysis and the fact that the chromogen o-dianisidine is quite toxic.

The glucose analysis having the highest specificity is generally considered to be the enzymatic determination with hexokinase/glucose 6-phosphate dehydrogenase. In this method, the glucose is phosphorylated with adenosine triphosphate/ hexokinase, and the thus-formed glucose 6-phosphate is dehydrogenated to gluconate 6-phosphate with glucose 6-phosphate dehydrogenase, wherein the hydrogen is transferred to nicotinamide adenine dinucleotide phosphate (NADP). The reduced coenzyme is then determined photometrically. Due to the central position of glucose 6-phosphate in the carbohydrate metabolism, this test is susceptible to disturbances by foreign enzymes, e.g., phosphoglucose isomerase, phosphoglucomutase and gluconate 6-phosphate dehydrogenase. Therefore, it is recommended to eliminate the interfering reactions by extrapolation. See H. U. Bergmeyer, "Methoden der enzymatischen Analyse" (Methods of Enzymatic Analysis), 2nd Ed. p. 1166, 1970, Chemie publishers, Weinheim. However, this makes the analytical method uncertain, cumbersome and time-consuming, e.g., about 20–30 minutes for a single determination.

It has now been found that the disadvantages of the methods heretofore employed in practice for the determination of glucose can be avoided by employing the novel glucose dehydrogenase enzymatic agent of this invention.

It was known from the pertinent literature (Methods of Enzymology, vol. IX, 92-111, Acad. Press New York, London, 1966; R. P. Metzger et al., J. Biol. Chem. 238, 1769-1772 (1964), and 240, 2767-2771 (1965); and N. G. Brink, Acta Chem. Scand. 7, 1081-1088 [1953]) that glucose dehydrogenase has a number of unfavorable properties which argue against the use thereof as an analytical agent. For example, frequently the glucose dehydrogenases are bound to particles and/or prove to be not dependent on NAD or NADP, respectively, Furthermore, it is known that glucose dehydrogenase has a low activity and/or too low a stability. The Michaelis constants of glucose dehydrogenase to glucose are only 0.007 – 2, i.e., only in a 0.007-molar solution is the enzyme saturated with substrate to the extent of one-half. However, during the usual blood sugar analysis, only about $10^{-7}$ mole of glucose is available. Consequently, there has been a considerable prejudice in the literature against the use of glucose dehydrogenase for enzymatic glucose analysis.

By means of the present invention, it is possible for the first time to provide an agent and a process for the enzymatic determination of glucose employing glucose dehydrogenase which yields rapid and reliable results with easy handling.

SUMMARY OF THE INVENTION

Accordingly, this invention relates to a novel agent for the enzymatic determination of glucose employing glucose dehydrogenase, a pyridine coenzyme and a buffer, with the formation of gluconic acid and reduced pyridine coenzyme, which comprises a mutarotation-accelerating substance and, optionally, an inhibitor for oxidases of reduced pyridine coenzymes and/or an alkali chloride.

In its process aspect, this invention relates to a process for the enzymatic determination of glucose, which comprises treating the glucose-containing sample to be analyzed with the agent of this invention and measuring the content of thus-formed reduced pyridine coenzyme in a conventional manner by spectrophotometry or fluorometry.

DETAILED DISCUSSION

The glucose determination agent of this invention is distinguished from the conventional agent employing the glucose oxidase method in that it measures specifically the glucose content and is not rendered inaccurate by other oxidizing or reducing agents. In contrast to the conventional hexokinase method, the novel agent has the advantage that only single-stage reaction is required, there being only one enzyme employed instead of the two employed in the hexokinase method. Since no indicator reaction is necessary, a possible interference caused thereby is likewise eliminated, which means a significant advantage over the glucose oxidase and hexokinase methods.

The determination requires, in a preferred embodiment, approximately 5 minutes, which makes this method twice as fast as the enzymatic glucose determination which is the most rapid at the present time, i.e., the hexokinase method without extrapolation of the disturbance reaction. The conversion time can be even further reduced considerably by increasing the enzyme activities in the test so that, in addition to the specificity, the smplicity as well as rapidity of the test according to the present invention are not achieved by any other glucose analysis.

Heretofore, glucose dehydrogenase, together with a mutarotation-accelerating substance, has never been utilized for glucose analysis. The reason appears to be found in the unfavorable properties described above of the glucose dehydrogenase presently available.

The glucose dehydrogenase employed in the enzymatic agent of this invention must be of maximum purity. The activities of glucose dehydrogenase utilized in the test are dependent predominantly on the time within which the end point of reaction is to be reached. However, the enzyme activity ca vary from about 2–200 U/ml. of testing solution. Preferably, 4–20 U/ml. of testing solution is employed together with the enzyme mutarotase.

The glucose dehydrogenase employed in this invention can be produced from microorganisms, preferably from a microorganism of the genus Bacillus, wherein the microbial starting compound contains a glucose dehydrogenase activity of at least 5 U/ml. of crude extract. The further purification thereof can be accomplished, for example, according to the method described in The Spores III, 97 (1965). In this way, lyophilized glucose dehydrogenase preparations are obtainble containing more than 2 U/mg. of dry substance, e.g., 2 to 20 U/mg., and the good solubility of which makes it possible to prepare solutions of more than 200 U/ml. in which the interfering dihydronicotinic acid amide adenine dinucleotide ($NADH_2$) oxidase activity amounts to less than 1‰ o (pro mille; 1‰ =0.1%) of the respective units of the glucose dehydrogenase activity.

The quality of the enzyme employed in this invention, which is better by several orders of magnitude compared to earlier-described preparations, makes it possible to use this enzyme for enzymatic glucose analysis.

The pyridine coenzyme or coenzymes contained in the agent of this invention is preferably nicotinamide adenine dinucleotide (NAD) or nicotinamide adenine dinucleotide phosphate (NADP), especially NAD. Other suitable pyridine coenzymes are, for example, thio-NAD, thio-NADP, nicotinamide purine dinucleotide, nicotinamide-(6-methyl-purine)-dinucleotide or nicotinamide-(2-chloro-6-methyl-purine)-dinucleotide.

The pyridine coenzyme concentration can be varied so as to provide about 2.0 millimole to 5.0 millimole concentration in the analytical test solution, without an effect on the speed of the reaction. In a preferred embodiment, the final concentration in the test solution is about 2.8 millimole NAD. In place of NAD and NAPD, it is also possible to utilize other NAD-active substances, such as, for example, thio-NAD or thio-NADP.

Since glucose dehydrogenase is specific for β-glucose, the α-glucose which is always present in equilibrium therewith must first mutarotate before it is converted by glucose dehydrogenase. In other words, at a high glucose dehydrogenase activity, the β-glucose present in the reaction mixture is rapidly consumed by the reaction, which is manifested by the steep ascent of the extinction at the beginning of the reaction. The gradual mutarotation of α-glucose to β-glucose is manifested by delayed $NADH_2$ formation, which is terminated only after more than 30 minutes. Therefore, the agent of this invention contains a mutarotation-accelerating substance, which increases the spontoneous mutarotation of α-glucose to β-glucose by more than 50%, preferably mutarotase. The acceleration of the mutarotation by the enzyme mutarotase for the glucose determination with glucose oxidase is known. J. Okuda, I. Miwa, Anal. Biochem. 43, 312 (1971). However, it was not obvious that, when adding mutarotase to the glucose dehydrogenase/NAD system, a very effective acceleration occurs as well. An amount of mutarotase corresponding numerically in units of activity to at least 8% of the glucose dehydrogenase activity is sufficient for optimal acceleration of the reaction. However, the mutarotase proportion can be increased as desired, without there being a negative influence on the test system.

In a preferred embodiment of the glucose determination, the ratio of mutarotase activity to glucose dehydrogenase activity is about 0.25 –1 : 10. A quantitative completion of the reaction within 5 minutes, which is a more than sixfold acceleration compared to the analogous testing system without mutarotase, is achieved, for example, with activities of 4 U of glucose dehydrogenase and 0.4 units of mutarotase per ml. of measured sample. With 20 U of glucose dehydrogenase and 2 units of mutarotase per ml. of testing solution, the reaction time is, for example, less than one minute. When using more than 100 U of glucose dehydrogenase and 10 units of mutarotase per ml. of testing solution, reaction times of the order of 10 seconds can be attained. However, in this case, the enzymes must be purified to a higher degree, or the interfering secondary activities must be suppressed.

The mutarotase can also be replaced by other substances exerting a mutarotation-accelerating effect on α-glucose. For example, when using a phosphate buffer in a concentration of 200 millimoles, the mutarotation-accelerating effect of the phosphate is fully utilized, and thereby more than 60% of the mutarotase activity can be saved. Further substances which have an accelerating on the mutarotation of α-glucose are, for example, histidine, imidazole, glutamic acid, aspartic acid, or α-hydroxypyridine. They are preferably employed in a concentration of 20–100 millimoles in the test and do not essentially affect the activity of glucose dehydrogenase in this concentration-range. However, mutarotase is preferably employed.

In order to achieve a rapid and quantitative glucose conversion, for the elimination and/or suppression of interfering secondary activities, and for the stabilization of glucose dehydrogenase, the agent of this invention optionally contains further components, e.g., inhibitors for oxidases of reduced pyridine coenzymes and/or an alkali chloride, e.g., lithium, sodium and/or potassium chloride.

In order to maintain the pH of the analytical liquid in a range of between about 6.5 and 8.5, preferably 7 to 8, the agent contains a buffer. The buffer is preferably employed in the test solution in a concentration of about 50–200 millimoles. Lower or higher concentrations are basically acceptable, insofar as the solubility of the various components is not reduced and the buffer capacity is sufficient in order to maintain the above-indicated pH range, i.e., the optimum range of the enzyme activity in the analytical sample. Suitable buffers are the compounds usually employed, which maintain the mixture at the above-mentioned pH of about 6.5 to 8.5, such as, for example, phosphate, tris(hydroxymethyl)aminomethane, diethanolamine, triethanolamine, collidine, borate, etc., preferably phosphate and tris buffers.

For measurements with high accuracy requirements, as demanded by glucose determinations in body fluids, the effect of a minor proportion of oxidases of reduced pyridine coenzymes can be seen. They have the effect that the thus-formed reduced pyridine coenzyme is again oxidized. Therefore, the extinction, serving as the measuring variable, does not remain constant but rather decreases again after reaching a maximum value. Additionally, the thus-measured maximum extinction is lower than the value calculated on the basis of the extinction coefficient of, for example, $NADH_2$ (about 3% – 5% too low with 1‰ $NADH_2$ oxidase). For this reason, it is advantageous if the agent of this invention also contains an inhibitor for oxidases of reduced pyridine coenzymes.

Since the preparative depletion of the residues of $NADH_2$ oxidase still present in the glucose dehydrogenase proved to be too complicated, it is advantageous to suppress the disturbing effect by the use of inhibitors for oxidases of reduced pyridine coenzymes. A number of inhibitors has now been found which effectively inhibits this interfering enzyme in relatively minor concentrations, without substantially affecting the activities of glucose dehydrogenase or mutarotase. These are especially pyridine derivatives purine derivatives and hydroxybenzoic acid derivatives.

Suitable are pyridine derivatives and pyridines substituted in at least one of the 2-, 3- and 4-positions by lower alkyl, phenyl, lower hydroxy-alkyl, lower haloalkyl, carboxy, lower acyl, benzoyl, carbonamide, and amino, and those having a benzene ring condensed in the 5,6-position of the pyridine ring. Examples of such derivatives are nicotinic acid, nicotinic acid amide, 2-amino-4-methyl-pyridine, 2-methyl-3-($\beta$-hydroxyethyl)-pyridine, 3-hydroxymethyl-pyridine, 2-hydroxymethylpyridine, 2-benzoylpyridine, quinolinic acid $\alpha$-methyl ester, 3-acetylquinoline, quinaldinic acid, quinolyl-2-chloromethane, quinaldine, 2-phenyl-quinolinic acid amide and/or "Atophan" (cinchopen). Preferably, 3-acetylquinoline, nicotinic acid, quinolyl-2-chloromethane, quinaldic acid and/or nicotinic acid amide are employed, especially 3-acetylquinoline.

Suitable purine derivatives are e.g., uric acid, caffeine, theophylline or purines bearing in the 2- and/or 6-positions hydroxy and/or amino groups and in the 7-position a ribose or deoxyribose group, such as, for example, xanthosine, 2-doexyguanosine, inosine, etc. Especially suitable in this group are xanthosine and/or uric acid.

Suitable hydroxybenzoic acid derivatives are those carrying a free or acylated hydroxy group in the 2- or 3-position and which can additionally be substituted by a sulfonic acid group, wherein the carboxyl group can also be present as an amide, such as, for example, m-hydroxybenzoic acid, salicylic acid, acetylsalicylic acid, salicylamide and/or sulfosalicylic acid, preferably 3-acetylquinoline and sulfosalicylic acid. Also well suitable proved to be 1-(p-chlorophenylsulfonyl)-3-propylurea. Particularly preferred is sulfosalicyclic acid, due to the strong inhibition of $NADH_2$ oxidase, the good solubility, the relatively minor effect on glucose dehyrogenase and mutarotase, the ready availability and the problem-free handling of this compound.

The content of $NADH_2$ oxidase inhibitor in the test system is variable and is dependent in each particular case on the existing activity of the interfering enzyme in the glucose dehydrogenase preparation. The inhibitors are advantageously present in the analytical agent in an amount which provides a final concentration in the analytical liquid of about 0.1 to 100 millimoles, preferably about 10–50 mM.

Optionally, the agent of this invention can also contain an alkali chloride, such as, for example, lithium, sodium and/or potassium chloride, particularly sodium chloride. It is known that the thermal stability of dissolved glucose dehydrogenase can be increased by the presence of sodium chloride. Glucose dehydrogenase solutions with a sodium chloride content of 3 M are shelf-stable for months when stored in a refrigerator. Since the enzyme is inhibited by the salt in case of sodium chloride concentrations of <0.8 M at a pH of 8.2, which is the pH value of the analytical liquid for the activity determination, stored solutions containing 3 M sodium chloride must be diluted for the activity determination. In this connection, surprisingly preparations whose activity has greatly decreased became reactivated by the salt. In an extreme case, an 86.4% loss of activity could be reversed. For the reactivation of the enzyme, it is necessary to maintain the sodium chloride concentration in the enzyme solution at least for one hour at 3 moles/liter prior to dilution of the solution. In order to achieve maximum reactivation of the glucose dehydrogenase, the sodium chloride concentration is preferably between 0.05 and 0.1 M. Preferably, a glucose dehydrogenase concentrate is utilized which is 2- to 5-molar, especially 3-molar with respect to the sodium chloride. For the glucose determination, the concentrate is diluted so that the sodium chloride concentration in the analytical liquid is 0.05- to 0.1-molar. In this way, one attains an optimum stability of the enzyme during storage, as well as an optimum activity in the analytical liquid.

The agent of this invention can additionally contain further components which are customarily employed for a diagnostic reagent. In order to avoid the formation of interfering air bubbles in the measuring cuvette, or for a more rapid dissolution of the solid substances, it is advisable, for example, to add a detergent or wetting agent in a concentration of between 0.01 an 0.1% by weight of the final test solution, for example, an ethoxylated glycerine monooleate or long-chain polyglycol ether.

The stability of the enzymes and reagents utilized makes it possible to mass-produce the testing system wherein the nicotinamide adenine dinucleotide is suitable freeze-dried, and the enzymes glucolse dehydrogenase and mutarotase are either freeze-dried or can also be provided as solutions. The enzymes can be premixed or separated and the buffer can, e.g., be present in the testing kit in solution with the $NADH_2$ oxidase inhibitor and the detergent. In this form, the testing system keeps at least for one year when stored in a refrigerator.

In order to conduct the test, the components present in the dry form are dissolved in an aqueous solvent, suitably only shortly prior to use, by adding the corresponding amount of solvent. The process of this invention is conducted by allowing the above-described agent to react with the glucose-containing sample to be analyzed, and measuring the content of thus-formed reduced pyridine coenzyme by spectrophotometry of fluorometry. For this purpose, the buffer solution, the enzyme mixture of glucose dehydrogenase and mutarotase, as well as the unknown sample, are mixed in a cuvette and the extinction $E_1$ and $E_{1(blank)}$ is read as soon as there is no longer a change in the extinction value. The blank sample contains distilled water instead of the sample solution. Thereafter, the reaction is initiated by adding the coenzyme solution. Once the extinction has become constant, $E_2$ and $E_{2(blank)}$ is measured and from the thus-obtained measured values, the glucose content of the specimen is calculated in accordance with Bucher (Hoppe-Seyler/Thierfelder, "Handbuch der Physiologisch- und Pathologisch-chemischen Analyse", 10th ed., Springer publishers, Berlin/Goettingen/Heidelberg/New York, pp. 292 et seq.).

The measuring temperature is not critical. However, it is recommended that the analysis be conducted at about 20°–40° C. and preferably at room temperature. The extinction measurements are made in the UV range between 300 and 400 nm., preferably at 366 nm. Instead of measuring the extinction in the UV range, it is also possible to determine the $NADH_2$ concentration in the sample by fluorometry. For this purpose, the excitation is effected at 366 nm. or at 313 nm. and 366 nm. and the fluoroescence emission is measured above 420 nm. Calibration is accomplished with gluclose solutions of known content.

In the determination of glucose in body fluids, such as, for example, blood, serum or plasma, or in other protein-containing specimens, it is advantageous to first conduct a deproteinization, employing the customary deproteinizing agents, such as, for example, trichloroacetic acid, perchloric acid or uranyl acetate/sodium chloride. However, a deproteinization of serum or plasma is not absolutely necessary.

The process of the present invention can also be conducted in automatic analyzers. For this purpose, the specimens to be analyzed are fed, via a specimen-collector, to an analytical system wherein the individual specimens are provided with the components of the agent of this invention. After mixing and after the reaction has been completed, the reaction solution is fed to a spectrophotometer and measured.

Test kits suitable for use in such automatic analyzers and also manual operations comprise, e.g., per hundred unknown or blank samples:

Reagent A glucose dehydrogenase ( 80 —2000 U) and
mutarotase ( 8 — 200 units),
as a solution in 10 — 12 ml. of buffered
(e.g., citrate pH 6.5)
2 — 5 M NaCl solution, or as a lyophilized
mixture in combination with a buffer solution,
e.g., 10 — 12 ml. of 100 mM (pH 6.5 — 8.5)
buffer, e.g., citrate.

Reagent B

Lyophilized NAD or NADP 0.4 — 1.5 mMol.

Solution A buffer, pH 6.5 – 8.5, e.g., 200 – 240 ml.
200 mM phosphate or 100 mM tris(hydroxymethyl) ainomethane.

Solution B (optional)

100 – 120 ml. deproteinizing agent, e.g.,
2 – 4 % aqueous trichloroacetic acid or
1 – 3 % aqueous perchloric acid The novel analytical agent of this invention can also be applied to absorbent substrates, i.e., carriers. Suitable absorbent substrates are all those which are customarily employed for instant testing. The most widely used is filter paper, but is also possible to utilize other absorbent cellulose or synthetic resin products. The absorbent substrates, preferably filter paper, are impregnated in a conventional manner with one or more impregnating solutions containing gluclose dehydrogenase, a tetrazolium salt a pyridine coenzyme, e.g., NAD, and a buffer system. There is no need to add mutarotase. Advantageous tetrazolium salts are 2-(p-iodophenyl)-3-(p-nitrophenyl)-5-phenyltetrazolium chloride (INT) and 3-(4,5-dimethylthiazolyl-1-2)-2,5-diphenyltetrazolium bromide (MTT).

The gluclose content of the solution to be investigated can be determined by the UV fluorescence of the thus-formed $NADH_2$. Alternatively, a subsequent color reaction indicating $NADH_2$ can be conducted. Suitably, the hydrogenation of a tetrazolium salt to the corresponding colored formazan is achieved with diaphorase.

Such test strips preferably have the following amounts per $mm^2$, of materials adsorbed thereon:
glucose dehydrogenase ( 10 – 25 ) $10^{-3}$ U;
nicotinamide adenine dinucleotide or
nicotinamide adenine dinucleotide
phosphate ( 0.8 – 3) $10^{-6}$ mMol.
tetrazolium salt (0.1 – 0.4) $10^{-3}$ mg.; and
buffer (pH 6.5 – 7.0) ( 0.1 – 5) $10^{-5}$ mMol.
diaphorase (0.6 – 30) $10^{-3}$U.

In addition to being used for the determination of glucose in biological fluids, e.g., blood, serum, plasma, urine, etc., the agent and process of this invention are likewise of great significance in industry, especially the food industry. Glucose determinations are of interest, for example, in the analysis of honey, fruit, jams, sweets, fruit juices, residual sweetness in wine, etc., as well as in sugar manufacture.

The invention will be explained in greater detail in the following examples.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

0.1 ml. of serum is deproteinized with 1 ml. of 3% strength trichloroacetic acid solution. Of the supernatant liquor, 0.2 ml. is added to 2 ml. of 0.1M tris buffer (pH 8.5), containing 0.5mM of 3-acetylquinoline in a cuvette. Thereafter, 0.1 ml. of an enzyme mixture containing 120 U GDH/ml. and 12 units of mutarotase/ml. in 0.05M citrate buffer (pH 6.5)/3M sodium chloride is added by pipette. The blank sample contains 0.2 ml. of the deproteinizing agent in place of the specimen solution. The analytical sample and blank sample are mixed and the extinctions are read off at 366 nm. after any changes in extinction have ceased (about 1–2 minutes).

The reaction is then initiated by adding 0.02 ml. of the aqueous coenzyme solution containing 0.58 M NAD. After about 5 minutes, the reaction is terminated and the extinctions are read off. From the thus-measured extinction difference ($\Delta E = 0.326$ at 366 nm.), a glucose content of 227 mg./100 ml. serum is calculated.

The same results are obtained using a 0.1M tris buffer solution containing, in place of 0.5 mM of 3-acetylquinoline, 45 mM of nicotinic acid, 1.6 mM of nicotinic acid amide, 0.4 mM of quinaldinic acid, or 0.13 mM of quinolyl-2-chloromethane.

The mutarotase units indicated in the test were determined as follows:

3 ml. of 0.1 M phosphate buffer (pH 7), containing 100 U peroxidase/ml. of buffer, 0.05 ml. of o-dianisidine solution (10 mg./ml. of water), 0.1 ml. of glucose oxidase solution (600 U/ml. of water), and 0.05 ml. of mutarotase solution of unknown activity are pipetted into a cuvette. By adding 0.1 ml. of freshly prepared α-glucose solution (0.3 mg./ml. of water), the reaction is initiated. The increase in extinction per minute ($\Delta E$) at 25° C. and 436 nm. is recorded. In the same manner, a blank value is determined, wherein water is employed instead of the mutarotase solution. The mutarotase activity is determined by the following formula:

$$\text{Mutarotase Units/ml. Enzyme Solution} = \frac{\Delta E - \Delta E_{blank}}{0.05}$$

EXAMPLE 2

0.02 ml. of serum is used directly in the reaction. The determination is effected analogously to Example 1. The following components are employed, in the sequence of addition: 2 ml. of 0.2M tris buffer (pH 7.3), containing 3 mM caffeine, 0.02 ml. of serum (or water in the case of the blank sample), 0.1 ml. of enzyme mixture, prepared by dissolving a lyophilized product in citrate buffer (pH 6.5), so that 120 U GDH/ml. and 12 units of mutarotase/ml. are present, and 0.02 ml. of an aqueous coenzyme solution, containing 0.32 M NAD.

After termination of the reaction (about 5 minutes), a glucose content of 96 mg./100 ml. of serum is calculated from the measured extinction difference $\Delta E = 0.164$.

The same results are obtained using a buffer solution containing, in place of 3 mM of caffeine, one of the following: 0.35 mM of uric acid, 21 mM of theophylline, 2.6 mM of deoxyguanosine, 30 mM of isosine, or 50 mM of xanthosine.

By employing, in place of the above enzymes, a highly purified enzyme mixture with 2500 U GDH/ml. and 250 units of mutarotase/ml., the reaction is complete in 10 seconds. The result is otherwise the same as above.

EXAMPLE 3

Urine is diluted with twice distilled H₂O in a ratio of 1 : 11 and 0.2 ml. of the thus-obtained specimen solution is utilized in the reaction. The analysis is conducted analogously to Example 1, the following components being employed in the sequence of their addition:

2 ml. of 0.1M phosphate buffer (pH 6.5), containing 40 mM of sulfosalicylic acid, 0.2 ml. of dilute urine (or water in cae of the blank sample), 0.1 ml. of a enzyme mixture containing 300 U GDH/ml. and 30 units of mutarotase/ml., dissolved in 0.05M citrate buffer (pH 6.5) which is 3M sodium chloride, and 0.02 ml. of aqueous coenzyme solution, containing 0.23 M NAD.

After about two minutes, the reaction is complete. The calculated extinction difference ($\Delta E = 0.305$) indicates a glucose content of 212 mg./100 ml. of urine.

The same results are obtained using buffer solution containing, in place of 40 mM of sulfosalicylic acid, any one of 1 mM of m-hydroxybenzoic acid, 0.5 mM of salicyclic acid, 0.7 mM of acetylsalicyclic acid, 10 mM of salicylamide, or 50 mM of 1-(p-chlorophenylsulfonyl)-3-propylurea.

EXAMPLE 4

A 54.0 mg. sample of honey is dissolved in twice distilled water to a volume of 100 ml. 0.2 ml. thereof is used for glucose analysis. The procedure is conducted analogously to Example 1, utilizing the following components, in the sequence in which they were added:

2 ml. of 0.2M phosphate buffer (pH 7.3), containing 40 mM of sulfosalicylic acid, 0.2 ml. of the solution to be analzyed (or water in case of the blank sample), 0.1 ml. of enzyme mixture, containing 300 U GDH/ml. and 20 units of mutarotase/ml., and 0.02 ml. of aqueous coenzyme solution, containing 0.32 M NAD or the corresponding amount of NADP.

After the reaction has terminated (about 2 minutes), an extinction difference of $\Delta E = 0.338$ is obtained. From this value, a glucose content of 21.4 mg. per 100 ml. of analytical solution is calculated. The honey thus contains 39.6% glucose.

EXAMPLE 5

A test kit for the enzymatic determination of glucose, sufficient for about 90 analyses and 10 blank values, contains the folloing components:

1. 110 ml. of a ready-for-use deproteinizing agent, viz., either a 3% aqueous solution of trichloroacetic acid, or a 2% aqueous solution of perchloric acid.
2. 220 ml. of a ready-for-use buffer, pH 7.3., viz., either 200 mM phosphate buffer or 100 mM tris(hydroxymethyl)aminomethane.
3. 11 ml. of a ready-for-use solution of GDH and mutarotase in 50 mM citrate buffer (pH 6.5)/3 M sodium chloride, or a lyophilized enzyme mixture of GDH and mutarotase which, for prior use, is dissolved in 11 ml. of 50 mM citrate buffer, in either case 120 U GDH/ml. and 12 units/ml. of mutarotase are present, i.e., a total of 1320 U of GDH and 132 units of mutarotase.
4. Lyophilized NAD or NADP which, at the time of use, is to be dissolved in 2.2 ml. of twice distilled water, resulting in a molarity of 330 mM.

The glucose determination with this test kit is conducted as described in the examples above.

EXAMPLE 6

For the production of test strips for a semiquantitative glucose analysis, the following components are dissolved in 20 ml. of 0.01M phosphate buffer (pH 6.5):

2150 U diaphorase (determined according to: H.U. Bergmeyer, "Methoden der Enzymatischen Analyse", 2nd edition, p. 406, Chemie publishers, Weinheim (1970),
1200 U GDH,
0.13 millimole NAD, and either
20 mg. of 2-(p-iodophenyl)-3-(p-nitrophenyl)-5-phenyltetrazolium chloride (INT), or
14 mg. of 3-(4,5-dimethylthiazolyl-1-2)-2,5-diphenyltetrazolium bromide (MTT).

The pH of the solution is adjusted, if necessary, to 6.5. Filter paper (Schleicher and Schuell No. 1450 CV) is impregnated with the reagent solution and dried in an air stream at 25° C. to provide a pick-up of about 0.25 $.10^{-3}$ ml./mm$^2$. The thus-obtained impregnated filter paper is dried and then cut into small squares of about 6 × 6 mm. and applied to one end of 6 × 60 mm. synthetic resin strips. Alternatively, it is advantageous to seal the absorbent substrate to a carrier foil prior to the impregnating step.

The thus-produced test strips are immersed for exactly 5 seconds in urine specimens of varying glucose contents and, after one minute, the formed color hue is evaluated with the aid of a color scale. Whereas there is a no color change in case of specimens without glucose, glucose concentrations of 50–100 mg. percent manifest themselves (when using INT) by a faint pink color (greyish-blue color with MTT); in the range of 250 mg. %, an intense pink color (blue with MTT); and above 500 mg. %, a red color (dark blue with MTT).

EXAMPLE 7

0.1 ml. of whole blood is deproteinized in 1.0 ml. of perchloric acid (2.0% by weight in twice distilled water). Analogously, 0.1 ml. of an aqueous glucose standard solution (100 mg. %) is mixed with 1.0 ml. of the deproteinizing agent. Employing a mechanized analysis system, the following pipetting operations are conducted:

2.0 ml. portions of a premixed buffer-enzyme mixture, pH 7.6, containing 0.12 M phosphate ions, 0.15 M NaCl, 20 U GDH/ml., and 2 units of mutarotase/ml. are mixed with 0.2 ml. of deproteinized sample (analysis) and with 0.2 ml. of perchloric acid standard solution (standard) and with 0.2 ml. of deproteinizing agent (blank sample), respectively. The reaction is initiated with 0.2 ml. respective portions of aqueous NAD solution (0.27M). After calibrating to 0, with blank sample, the extinction of the standard $E_S$ and the analysis sample $E_A$ is determined at 366 nm. after an incubating period of 5 minutes.

The thus-measured extinction values $E_S = 0.150$ and $E_A = 0.439$ are printed out. The glucose concentration of the sample is calculated therefrom in a conventional manner to be 293 mg.%.

The same result is obtained when conducting the analysis in devices operating according to the flow principle (continuous flow) or with centrifugal force. The calculation of the glucose concentration in the specimen is effected in this case with a calibration curve obtained by analysis of a series of standard solutions of different glucose concentrations.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An analytical agent for the quantitative enzymatic determination of glucose, consisting essentially of:
   a. glucose dehydrogenase having a dry weight activity of at least 2 U/mg., the NAOH$_2$ oxidase activity of which is less than 0.1% of said glucose dehydrogenase activity;
   b. a pyridine coenzyme selected from the group consisting of NAD, NADP, thio-NAD, thio-NADP, nicotinamide purine dinucleotide, nicotinamide-(6-methylpurine)-dinucleotide and nicotinamide-(2-chloro-6-methylpurine)-dinucleotide in an amount sufficient to provide about a 2.0–5.0 millimole concentration in an analytical test solution;
   c. means for maintaining an aqueous test solution of said analytical agent at a pH of about 6.5–8.5; and
   d. mutarotase in an amount sufficient to increase the spontaneous mutarotation of α-glucose to β-glucose in said test solution by more than 50%.

2. An analytical agent according to claim 1, further comprising an inhibitor for oxidase of reduced pyridine coenzymes.

3. An analytical agent according to claim 1, further comprising a thermal stabilizing amount of an alkali metal chloride.

4. An analytical agent according to claim 3, wherein the alkali chloride is sodium chloride.

5. An analytical agent according to claim 1, wherein said pyridine coenzyme is NAD or NADP.

6. An analytical agent according to claim 1, wherein the ratio of mutarotase activity to glucose dehydrogenase activity is about 0.25–1 : 10.

7. An analytical agent according to claim 6, wherein said pyridine coenzyme is NAD or NADP.

8. An analytical agent according to claim 7, further comprising a thermal stabilizing amount of sodium chloride.

9. An analytical agent according to claim 8, wherein said pyridine coenzyme is NAD.

10. A process for the quantitative enzymatic determination of glucose, which comprises reacting a glucose-containing test solution with an analytical agent according to claim 1 to reduce the pyridine coenzyme therein and measuring the concentration of the resultant reduced pyridine coenzyme by spectrophotometry or fluorometry.

* * * * *